(12) United States Patent
Famodu et al.

(10) Patent No.: US 6,653,099 B1
(45) Date of Patent: Nov. 25, 2003

(54) PLANT UDP-GLUCOSE DEHYDROGENASE

(75) Inventors: Omolayo O. Famodu, Newark, DE (US); Emil M. Orozco, Jr., Cochranville, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/429,906

(22) Filed: Oct. 29, 1999

Related U.S. Application Data

(60) Provisional application No. 60/107,274, filed on Nov. 5, 1998.

(51) Int. Cl.⁷ ............... C12P 21/00; C07H 21/04
(52) U.S. Cl. .............. 435/69.1; 435/419; 435/468; 536/23.2; 536/23.6; 800/284; 800/295
(58) Field of Search .................. 435/471, 468, 435/320.1, 419, 430, 69.1; 536/23.2, 23.6; 800/284, 295

(56) References Cited

FOREIGN PATENT DOCUMENTS

| CA | 2 180 786 A | | 1/1998 |
|---|---|---|---|
| WO | WO97/12983 A | | 4/1997 |
| WO | WO99/29875 | * | 6/1999 |

OTHER PUBLICATIONS

Berendsen A Glimpse of the Holy Grail 1998 vol. 282 Science pp. 642–643.*
Kinnaird, J.H. et al., EMBL Accession No. K01409, Jun. 13, 1995—XP002136231 1985.
Sakakibara Hitoshi et al., Journ. of Bio. Chem., vol. 271(47):29561–29568—XP002136232 1996.
Mckenzie et al., Database Accession No. PREV198273042087—XP002136239—Biosciences Info. Service 1981 Archives of Biochem. & Biophys., 1981, vol. 212(1):290–297.
Cooke, R. et al., EMBL Accession No. F20094, Mar. 5, 1996—XP002136233.
Cooke, R. et al., EMBL Accession No. F20093, Mar.5, 1996—XP002136234.
Turano Frank J. et al., Database Accession No. PREV199800409360—XP002136240 Plant Science, 1998, vol. 135(2):137–148.
Saigusa, M. et al., Database Accession No. PREV197458004768—XP002136241 Soil Science and Plant Nutrition, 1973, vol. 18(2):125–132.
Gil 'Manov M.K. et al., Database Accession No. PREV198988042880—XP002136242 Doklady Akademii Nauk SSSR, 1988, vol. 303(4):987–989.
Hadzi–Taskovic–Sukalovic V, 1990, Database Accession No. PREV199191032155—XP002136243 Physiologia Plantarum, 1990, vol. 80(2):238–242.
Quetz, P–C et al., 1982, Database Accession No. PREV198376029397—XP002136273 Biochemie and Physiologie Der Pflanzen, 1982, vol. 177(7):567–576.
Wen, Z. et al., EMBL Accession No. U82240—Jan. 12, 1997, XP002136235.
Wen, Z. et al., Appln. Environ. Microbiol. 62(10):3826–3833—XP002136236 1996.
Rounsley, S.D.–EMBL Accession No. B22305—Oct. 13, 1997—XP002136237.
Rounsley, S.D. et al., EMBL Accession No. B25235, Oct. 13, 1997, XP002136238.
Anderson, Bruce M. et al., Database Accession No. PREV199395089827—XP002136244 Archives of Biochemistry & Biophysics, 1993, vol. 300(1):483–488.
Sakaibara Hitoshi et al., Database Accession No. PREV199598452191—XP002136245 Plant and Cell Physiology, 1995, vol. 36(5):789–797.
Cramer et al. (1998) The American Society of Plant Physiologists Meeting).
NCBI General Identifier No. 1518540 1997.
Tenhaken et al., (1996), Plant Physiol., 112(3):1127–1134 (MEDLINE 97092851).

* cited by examiner

*Primary Examiner*—James Ketter
*Assistant Examiner*—Daniel M Sullivan

(57) ABSTRACT

This invention relates to an isolated nucleic acid fragment encoding a hemicellulose biosynthesis protein. The invention also relates to the construction of a chimeric gene encoding all or a portion of the hemicellulose biosynthesis protein, in sense or antisense orientation, wherein expression of the chimeric gene results in production of altered levels of the hemicellulose biosynthesis protein in a transformed host cell.

11 Claims, No Drawings

SEQUENCE LISTING

```
<160> NUMBER OF SEQ ID NOS:  8

<210> SEQ ID NO 1
<211> LENGTH: 546
<212> TYPE: DNA
<213> ORGANISM: Oryza sp.
<220> FEATURE:
<221> NAME/KEY: unsure
<222> LOCATION: (421)
<221> NAME/KEY: unsure
<222> LOCATION: (425)
<221> NAME/KEY: unsure
<222> LOCATION: (447)
<221> NAME/KEY: unsure
<222> LOCATION: (467)
<221> NAME/KEY: unsure
<222> LOCATION: (483)
<221> NAME/KEY: unsure
<222> LOCATION: (523)
<221> NAME/KEY: unsure
<222> LOCATION: (527)

<400> SEQUENCE: 1
```

-continued

```
gctcccagtc caaacatttc tcctcctcgg tctggagccg ttctcccccc tccccgccgc    60
cgctgctctc gacgccgacg ccgacgaggc agctaggccg gcgacgaacc tcgatctcga   120
tccgctcgcc gccgtccgtc gccgatccgc gcgccgacac cgacaccgac cttgatcctg   180
atccgcgctc cccgcgacgt acgccacggt ttgcaagtaa gcaggaaaga tggtgaagat   240
ctgctgcatc ggagctggat atgtcggcgg cccaaccatg gctgtcattg ccctcaaatg   300
cccagcaatt gaggtggtgg ttgttgacat ctccaagctt cgcgttgatg cctggaacaa   360
cgaccaactc ccaatctacg aacccggtct tgatgaggtt gtgaaggaat gcaaggggaa   420
ngaanctctt ccttagtacg gacgtcnaag aaacaagtcg ctgaagnaag acatcatctt   480
tgngtccgtc aaaccctaa caaagaaccg tgggaccttg ganaagnaaa ggttgctgac   540
ctcaac                                                              546
```

```
<210> SEQ ID NO 2
<211> LENGTH: 72
<212> TYPE: PRT
<213> ORGANISM: Oryza sp.
<220> FEATURE:
<221> NAME/KEY: UNSURE
<222> LOCATION: (64)
<221> NAME/KEY: UNSURE
<222> LOCATION: (65)

<400> SEQUENCE: 2
```

Met Val Lys Ile Cys Cys Ile Gly Ala Gly Tyr Val Gly Gly Pro Thr
  1               5                  10                  15

Met Ala Val Ile Ala Leu Lys Cys Pro Ala Ile Glu Val Val Val Val
                 20                  25                  30

Asp Ile Ser Lys Leu Arg Val Asp Ala Trp Asn Asn Asp Gln Leu Pro
             35                  40                  45

Ile Tyr Glu Pro Gly Leu Asp Glu Val Val Arg Asn Ala Arg Gly Xaa
         50                  55                  60

Xaa Leu Phe Leu Ser Thr Asp Val
 65                  70

```
<210> SEQ ID NO 3
<211> LENGTH: 636
<212> TYPE: DNA
<213> ORGANISM: Triticum sp.
<220> FEATURE:
<221> NAME/KEY: unsure
<222> LOCATION: (284)
<221> NAME/KEY: unsure
<222> LOCATION: (395)
<221> NAME/KEY: unsure
<222> LOCATION: (434)
<221> NAME/KEY: unsure
<222> LOCATION: (440)
<221> NAME/KEY: unsure
<222> LOCATION: (441)
<221> NAME/KEY: unsure
<222> LOCATION: (464)
<221> NAME/KEY: unsure
<222> LOCATION: (478)
<221> NAME/KEY: unsure
<222> LOCATION: (492)
<221> NAME/KEY: unsure
<222> LOCATION: (506)
<221> NAME/KEY: unsure
<222> LOCATION: (507)
<221> NAME/KEY: unsure
<222> LOCATION: (512)
<221> NAME/KEY: unsure
<222> LOCATION: (518)
```

<221> NAME/KEY: unsure
<222> LOCATION: (542)
<221> NAME/KEY: unsure
<222> LOCATION: (564)
<221> NAME/KEY: unsure
<222> LOCATION: (569)
<221> NAME/KEY: unsure
<222> LOCATION: (607)

<400> SEQUENCE: 3

| | | | | | |
|---|---|---|---|---|---|
| tccaccaaga | agtcgcctcc | gttgctttcc | tccagcagtg | cgcgccctc | ctctcgagat | 60 |
| cttctccgag | ttcctgagat | ctggttgtaa | gcagccaaga | tggtgaagat | ctgctgcatc | 120 |
| ggagctggct | acgtcggcgg | cccaaccatg | gctgtcattg | ccatcaagtg | cccggcgatt | 180 |
| gaggtggtgg | ttgtggacat | ctccaagccc | cgcattgacg | cctggaacag | cgacaccctc | 240 |
| ccgatctacg | agcccggcct | cgatgatgtt | gtcaaggcct | gcangggaa | gaacctcttc | 300 |
| ttcagcactg | atgttgagaa | gcatgtcgcc | gaggccgaca | tcatcttcgt | ctccgtgaac | 360 |
| accccacaaa | gacccgcggt | ctggaaccgg | aaagntgccg | acctcactac | tgggaaaacg | 420 |
| ccgcccggat | gatnccgacn | ntcaagtcga | caaatgtctc | agantcaacg | tccttaanac | 480 |
| gcgaggcatt | anaaatctga | ccacanncag | gnacactnca | aatctgtcac | cgggttcccc | 540 |
| tnaggaacgc | atcaggactg | taanccaana | tgtatcgtgg | cggaaccggg | gaaaagctca | 600 |
| gcccagngtt | ccatggtcca | gaaaatataa | cacgtg | | | 636 |

<210> SEQ ID NO 4
<211> LENGTH: 95
<212> TYPE: PRT
<213> ORGANISM: Triticum sp.
<220> FEATURE:
<221> NAME/KEY: UNSURE
<222> LOCATION: (62)

<400> SEQUENCE: 4

Met Val Lys Ile Cys Cys Ile Gly Ala Gly Tyr Val Gly Gly Pro Thr
  1               5                  10                  15
Met Ala Val Ile Ala Ile Lys Cys Pro Ala Ile Glu Val Val Val
                 20                  25                  30
Asp Ile Ser Lys Pro Arg Ile Asp Ala Trp Asn Ser Asp Thr Leu Pro
             35                  40                  45
Ile Tyr Glu Pro Gly Leu Asp Asp Val Val Lys Ala Cys Xaa Gly Lys
         50                  55                  60
Asn Leu Phe Phe Ser Thr Asp Val Glu Lys His Val Ala Glu Ala Asp
 65                  70                  75                  80
Ile Ile Phe Val Ser Val Asn Thr Pro Thr Lys Thr Arg Gly Leu
                 85                  90                  95

<210> SEQ ID NO 5
<211> LENGTH: 1931
<212> TYPE: DNA
<213> ORGANISM: Oryza sativa

<400> SEQUENCE: 5

| | | | | | |
|---|---|---|---|---|---|
| gctcccagtc | caaacatttc | tcctcctcgg | tctggagccg | ttctcccccc | tcccgccgc | 60 |
| cgctgctctc | gacgccgacg | ccgacgaggc | agctaggccg | gcgacgaacc | tcgatctcga | 120 |
| tccgctcgcc | gccgtccgtc | gccgatccgc | gcgccgacac | cgacaccgac | cttgatcctg | 180 |
| atccgcgctc | cccgcgacgt | acgccacggt | ttgcagtaag | caggaaagat | ggtgaagatc | 240 |
| tgctgcatcg | gagctggata | tgtcggcggc | ccaaccatgg | ctgtcattgc | cctcaaatgc | 300 |

-continued

```
ccagcaattg aggtggtggt tgttgacatc tccaagcttc gcgttgatgc ctggaacagc    360
gaccagctcc caatctacga gcccggtctt gatgaggttg tgaaggaatg cagggggcagg   420 aacctcttct tcagtacgga cgtcgagaag catgtcgctg aggcagacat catctttgtg    480
tctgtcaaca cccctaccaa gacccgtgga cttggagcag gcaaggctgc tgacctcacc    540
tactgggaga gtgctgctcg gatgattgct gatgtctcca gtctgacaa gatcgttgtt    600 gagaagtcca ctgtccctgt caagactgca gaggccattg agaagatctt gacccacaac    660
agcaagggca tcaactacca gatcctctcc aacccagaat tccttgcaga gggcactgcg    720
attgaagatc tcttcaagcc agacagagtg ctcattggtg ccgggagac tcctgaagga    780 aagaaggctg ttcaggctct caaggaagtt tatgcccatt gggttcctga ggacaggatt    840
atcaccacca acctgtggtc tgctgagctc tccaagctcg cagccaatgc gttcttggcg    900
cagagaatct cctctgtgaa tgccatctct gcactatgtg aggcgactgg tgccaatgtg    960
tccgaggtgg cctatgctgt ggggaaagac accagaatcg gccccaagtt cttgaatgcc    1020
agtgtcggct tggtggctc ctgtttccag aaggacatcc tgaacctcgt gtacatctgc    1080
gagtgcaatg ccttcctga ggttgccaac tactggaagc aggtcatcaa gattaacgac    1140
taccagaaga gccggtttgt caaccgtgtt gtggcctcca tgttcaacac tgtctctggc    1200
aagaagattg ccgtccttgg ctttgcgttc aagaaggaca ccggtgacac cagggagaca    1260
cctgccattg atgtgtgcca tggcctgttg ggtgacaagg ctcaaatcag catctacgac    1320
ccacaggtaa ctgaagatca gatccagcgg gacctttcca tggccaagtt tgattgggac    1380
cacccaaggc acctgcagcc aactagcccc acggctttta agcaggtgag tgtggtctgg    1440
gatgcgtatg aggccaccaa gggagcccat ggactgtgca tcctcactga gtgggacgag    1500
ttcaagacct tggactacca gaggatcttt gacaacatgc agaaacctgc atttgtcttc    1560
gatgggcgca atgtggtcga tcctgagaag ctcagggaga ttggcttcat tgtctactct    1620
attggcaagc cgcttgatgc atggctcaaa gacatgcccg cggttgcata attctgaatc    1680
cccacctgga gcgctctgct ggagctgaag aaattcgata aggaaacaga accggtcgac    1740
cactattttc tgtagtctgt ttttgcagga gacagctacc attttctcag tcgtaagttg    1800
aatatctgtt agtatctttg tcgaagttt catgtttgca gctttgcgcc tttgtagatc    1860
tgaaatcctc aagcctctgc tctaagagtg ccacccaaaa tacctcttgt atcaaaaaaa    1920
aaaaaaaaaa a                                                        1931
```

<210> SEQ ID NO 6
<211> LENGTH: 480
<212> TYPE: PRT
<213> ORGANISM: Oryza sativa

<400> SEQUENCE: 6

Met Val Lys Ile Cys Cys Ile Gly Ala Gly Tyr Val Gly Gly Pro Thr
1               5                   10                  15

Met Ala Val Ile Ala Leu Lys Cys Pro Ala Ile Glu Val Val Val
            20                  25                  30

Asp Ile Ser Lys Leu Arg Val Asp Ala Trp Asn Ser Asp Gln Leu Pro
        35                  40                  45

Ile Tyr Glu Pro Gly Leu Asp Glu Val Val Lys Glu Cys Arg Gly Arg
    50                  55                  60

Asn Leu Phe Phe Ser Thr Asp Val Glu Lys His Val Ala Glu Ala Asp
65                  70                  75                  80

-continued

```
Ile Ile Phe Val Ser Val Asn Thr Pro Thr Lys Thr Arg Gly Leu Gly
                85                  90                  95

Ala Gly Lys Ala Ala Asp Leu Thr Tyr Trp Glu Ser Ala Ala Arg Met
            100                 105                 110

Ile Ala Asp Val Ser Lys Ser Asp Lys Ile Val Val Glu Lys Ser Thr
        115                 120                 125

Val Pro Val Lys Thr Ala Glu Ala Ile Glu Lys Ile Leu Thr His Asn
    130                 135                 140

Ser Lys Gly Ile Asn Tyr Gln Ile Leu Ser Asn Pro Glu Phe Leu Ala
145                 150                 155                 160

Glu Gly Thr Ala Ile Glu Asp Leu Phe Lys Pro Asp Arg Val Leu Ile
                165                 170                 175

Gly Gly Arg Glu Thr Pro Glu Gly Lys Lys Ala Val Gln Ala Leu Lys
            180                 185                 190

Glu Val Tyr Ala His Trp Val Pro Glu Asp Arg Ile Ile Thr Thr Asn
        195                 200                 205

Leu Trp Ser Ala Glu Leu Ser Lys Leu Ala Ala Asn Ala Phe Leu Ala
    210                 215                 220

Gln Arg Ile Ser Ser Val Asn Ala Ile Ser Ala Leu Cys Glu Ala Thr
225                 230                 235                 240

Gly Ala Asn Val Ser Glu Val Ala Tyr Ala Val Gly Lys Asp Thr Arg
                245                 250                 255

Ile Gly Pro Lys Phe Leu Asn Ala Ser Val Gly Phe Gly Gly Ser Cys
            260                 265                 270

Phe Gln Lys Asp Ile Leu Asn Leu Val Tyr Ile Cys Glu Cys Asn Gly
        275                 280                 285

Leu Pro Glu Val Ala Asn Tyr Trp Lys Gln Val Ile Lys Ile Asn Asp
    290                 295                 300

Tyr Gln Lys Ser Arg Phe Val Asn Arg Val Val Ala Ser Met Phe Asn
305                 310                 315                 320

Thr Val Ser Gly Lys Lys Ile Ala Val Leu Gly Phe Ala Phe Lys Lys
                325                 330                 335

Asp Thr Gly Asp Thr Arg Glu Thr Pro Ala Ile Asp Val Cys His Gly
            340                 345                 350

Leu Leu Gly Asp Lys Ala Gln Ile Ser Ile Tyr Asp Pro Gln Val Thr
        355                 360                 365

Glu Asp Gln Ile Gln Arg Asp Leu Ser Met Ala Lys Phe Asp Trp Asp
    370                 375                 380

His Pro Arg His Leu Gln Pro Thr Ser Pro Thr Ala Phe Lys Gln Val
385                 390                 395                 400

Ser Val Val Trp Asp Ala Tyr Glu Ala Thr Lys Gly Ala His Gly Leu
                405                 410                 415

Cys Ile Leu Thr Glu Trp Asp Glu Phe Lys Thr Leu Asp Tyr Gln Arg
            420                 425                 430

Ile Phe Asp Asn Met Gln Lys Pro Ala Phe Val Phe Asp Gly Arg Asn
        435                 440                 445

Val Val Asp Pro Glu Lys Leu Arg Glu Ile Gly Phe Ile Val Tyr Ser
    450                 455                 460

Ile Gly Lys Pro Leu Asp Ala Trp Leu Lys Asp Met Pro Ala Val Ala
465                 470                 475                 480

<210> SEQ ID NO 7
<211> LENGTH: 1858
```

<210> SEQ ID NO 7
<211> LENGTH: 1858
<212> TYPE: DNA
<213> ORGANISM: Triticum aestivum

<400> SEQUENCE: 7

| | | |
|---|---|---|
| cttctctgca tccaccaaga agtcgcctcc gttgctttcc tccagcagtg cgcgcccctc | 60 |
| ctctcgagat cttctccgag ttcctgagat ctggttgtaa gcagccaaga tggtgaagat | 120 |
| ctgctgcatc ggagctggct acgtcggcgg cccaaccatg ctgtcattg ccatcaagtg | 180 |
| cccggcgatt gaggtggtgg ttgtggacat ctccaagccc cgcattgacg cctggaacag | 240 |
| cgacaccctc ccgatctacg agcccggcct cgatgatgtt gtcaaggcct gcaggggaa | 300 |
| gaacctcttc ttcagcactg atgttgagaa gcatgtcgcc gaggccgaca tcatcttcgt | 360 |
| ctccgtgaac accccacca agacccgcgg tctgggagcc ggcaaggctg ccgacctcac | 420 |
| ctactgggag agcgccgccc ggatgatcgc cgacgtgtcc aagtccgaca agatcgtcgt | 480 |
| cgagaagtcc accgtccctg tcaagaccgc cgaggccatt gagaagatcc tgacccacaa | 540 |
| cagcaagggc atcaactacc agatcctgtc caacccggag ttcctcgctg agggcaccgc | 600 |
| catcgaggac ctgttcaagc ccgacagagt gctcatcggt ggccgggaga cccccggggg | 660 |
| ccagaaggcc gtccaggccc tcaaggaggt gtacgcccac tgggtccccg aggagaacat | 720 |
| catcaccacc aacctgtggt ctgccgagct ctccaagctc gccgccaacg cgttcttggc | 780 |
| ccagaggatc tcgtccgtga acgccatgtc ggcgctctgc gaggccaccg cgccaacgt | 840 |
| gtcggaggtg tcgtacgcca tcggcaagga ctcgaggatc gggcccaagt tcctgaacgc | 900 |
| cagcgtgggg ttcggcgggt cgtgcttcca gaaggacatc ctgaacctgg tgtacatctg | 960 |
| cgagtgcaac ggcctgccgg aggtggccaa ctactggaag caggtgatca agatcaacga | 1020 |
| ctaccagaag agccggttcg tgaaccgcgt ggtgtcgtcc atgttcaaca cggtgtccgg | 1080 |
| caagaagatc gccgtgctcg ggttcgcctt caagaaggac acgggcgaca cccgggagac | 1140 |
| gccggcgatc gacgtgtgca agggcctggt gggcgacaag gcccaggtga gcatctacga | 1200 |
| cccgcaggtg acggaggatc agatccagcg ggacctggcc atgaacaagt cgactgggga | 1260 |
| ccacccgatg cacctgcagc cgaccagccc cacgcggtg aagcaggtga gcgtggtgtg | 1320 |
| ggacgcgtac gaggccgcca agggcgccca cggcgtgtgc atcctcaccg agtgggacga | 1380 |
| gttcaagaag ctcgactacc agaagatctt cgacaacatg cagaagcccg ccttcgtgtt | 1440 |
| tgacggccgc aacgtcgtcg acgccgagaa gctcagggag atcggcttca tcgtctactc | 1500 |
| catcggcaag ccgtcgacg gctggctcaa ggacatgccc gccgtggcct aagttcacct | 1560 |
| cgtcggccgg ccggatcgga ggaagagcaa gaagtggttt gaccgtgatt cattctttat | 1620 |
| agtttgcatt ttgcaggaga agcatccaca ttttctctct cggccataag aatttagtaa | 1680 |
| atcttcatgt cttgttaagt ttccgataca tgtttgcgcc accccgtctg tagatcttac | 1740 |
| ttataatcaa atcctcgggc ccctgtgctg cctgaggagg tttttccgtt gtatcccatg | 1800 |
| aacgaacttt gtagcctgtt ttgctgaaat cattacagaa tccaatgtgt tttttcaa | 1858 |

<210> SEQ ID NO 8
<211> LENGTH: 480
<212> TYPE: PRT
<213> ORGANISM: Triticum aestivum

<400> SEQUENCE: 8

Met Val Lys Ile Cys Cys Ile Gly Ala Gly Tyr Val Gly Gly Pro Thr
 1               5                  10                  15

Met Ala Val Ile Ala Ile Lys Cys Pro Ala Ile Glu Val Val Val Val

-continued

```
                20                  25                  30
Asp Ile Ser Lys Pro Arg Ile Asp Ala Trp Asn Ser Asp Thr Leu Pro
            35                  40                  45
Ile Tyr Glu Pro Gly Leu Asp Asp Val Val Lys Ala Cys Arg Gly Lys
 50                  55                  60
Asn Leu Phe Phe Ser Thr Asp Val Glu Lys His Val Ala Glu Ala Asp
 65                  70                  75                  80
Ile Ile Phe Val Ser Val Asn Thr Pro Thr Lys Thr Arg Gly Leu Gly
                85                  90                  95
Ala Gly Lys Ala Ala Asp Leu Thr Tyr Trp Glu Ser Ala Ala Arg Met
            100                 105                 110
Ile Ala Asp Val Ser Lys Ser Asp Lys Ile Val Glu Lys Ser Thr
            115                 120                 125
Val Pro Val Lys Thr Ala Glu Ala Ile Glu Lys Ile Leu Thr His Asn
130                 135                 140
Ser Lys Gly Ile Asn Tyr Gln Ile Leu Ser Asn Pro Glu Phe Leu Ala
145                 150                 155                 160
Glu Gly Thr Ala Ile Glu Asp Leu Phe Lys Pro Asp Arg Val Leu Ile
                165                 170                 175
Gly Gly Arg Glu Thr Pro Gly Gly Gln Lys Ala Val Gln Ala Leu Lys
            180                 185                 190
Glu Val Tyr Ala His Trp Val Pro Glu Glu Asn Ile Ile Thr Thr Asn
            195                 200                 205
Leu Trp Ser Ala Glu Leu Ser Lys Leu Ala Ala Asn Ala Phe Leu Ala
210                 215                 220
Gln Arg Ile Ser Ser Val Asn Ala Met Ser Ala Leu Cys Glu Ala Thr
225                 230                 235                 240
Gly Ala Asn Val Ser Glu Val Ser Tyr Ala Ile Gly Lys Asp Ser Arg
                245                 250                 255
Ile Gly Pro Lys Phe Leu Asn Ala Ser Val Gly Phe Gly Gly Ser Cys
            260                 265                 270
Phe Gln Lys Asp Ile Leu Asn Leu Val Tyr Ile Cys Glu Cys Asn Gly
            275                 280                 285
Leu Pro Glu Val Ala Asn Tyr Trp Lys Gln Val Ile Lys Ile Asn Asp
            290                 295                 300
Tyr Gln Lys Ser Arg Phe Val Asn Arg Val Val Ser Ser Met Phe Asn
305                 310                 315                 320
Thr Val Ser Gly Lys Lys Ile Ala Val Leu Gly Phe Ala Phe Lys Lys
                325                 330                 335
Asp Thr Gly Asp Thr Arg Glu Thr Pro Ala Ile Asp Val Cys Lys Gly
            340                 345                 350
Leu Val Gly Asp Lys Ala Gln Val Ser Ile Tyr Asp Pro Gln Val Thr
            355                 360                 365
Glu Asp Gln Ile Gln Arg Asp Leu Ala Met Asn Lys Phe Asp Trp Asp
370                 375                 380
His Pro Met His Leu Gln Pro Thr Ser Pro Thr Ala Val Lys Gln Val
385                 390                 395                 400
Ser Val Val Trp Asp Ala Tyr Glu Ala Ala Lys Gly Ala His Gly Val
                405                 410                 415
Cys Ile Leu Thr Glu Trp Asp Glu Phe Lys Lys Leu Asp Tyr Gln Lys
            420                 425                 430
Ile Phe Asp Asn Met Gln Lys Pro Ala Phe Val Phe Asp Gly Arg Asn
            435                 440                 445
```

```
Val Val Asp Ala Glu Lys Leu Arg Glu Ile Gly Phe Ile Val Tyr Ser
    450                 455                 460
Ile Gly Lys Pro Leu Asp Gly Trp Leu Lys Asp Met Pro Ala Val Ala
465                 470                 475                 480
```

PLANT UDP-GLUCOSE DEHYDROGENASE

This application claims priority benefit of U.S. Provisional Application No. 60/107,274 filed Nov. 5, 1998, now expired.

FIELD OF THE INVENTION

This invention is in the field of plant molecular biology. More specifically, this invention pertains to nucleic acid fragments encoding proteins involved in hemicellulose production in plants and seeds.

BACKGROUND OF THE INVENTION

UDP-glucuronic acid a precursor of hemicellulose. Hemicellulose is a major component of primary plant cell walls. Many of the glycosyl residues found in hemicellulose are derived from the sugar precursor UDP-glucuronic acid, which can be converted into UDP-arabinose, UDP-apiose, UDP-galacturonic acid, and UDP-xylose. The synthesis of non-cellulosic cell wall polysaccharides, a major component of plant cell walls, is directed through the enzyme, UDP-glucose dehydrogenase. This enzyme has been shown to be the rate limiting step in the biosynthesis of non-cellulosic polysaccharides, suggesting it is a key regulatory step in cell wall synthesis. It has been shown that over expression of UDP-glucose dehydrogenase in transgenic plants caused a 50% increase in leaf elongation rate (LER) compared to wildtype (Cramer, G. R., et al., (1998) The American Society of Plant Physiologists Annual Meeting, Session #39, Abstract #332). The enzyme is highly expressed in young roots, but lower expression levels have been observed in expanding tissues of the epicotyl and in young leaves. The expression pattern of the enzyme in different developmental stages strengthens the argument that UDP-glucose dehydrogenase is a key regulator for the availability of hemicellulose precursors. Thus, it appears that biosynthesis of cell wall components is a rate-limiting step for cell expansion and plant growth and that UDP-glucose dehydrogenase may be powerful new tool to manipulate the growth of plants.

SUMMARY OF THE INVENTION

The present invention relates to isolated polynucleotides comprising a nucleotide sequence encoding a first polypeptide of at least 70 amino acids, preferably 480 amino acids, that has at least 96% identity based on the Clustal method of alignment when compared to a polypeptide selected from the group consisting of a rice UDP-glucose dehydrogenase polypeptide of SEQ ID NO:6, and a wheat UDP-glucose dehydrogenase polypeptide of SEQ ID NO:8. The present invention also relates to an isolated polynucleotide comprising the complement of the nucleotide sequences described above.

The present invention relates to isolated polynucleotides comprising a nucleotide sequence encoding a first polypeptide of at least 70 amino acids, preferably 480 amino acids, that has at least 94%, preferably 96%, identity based on the Clustal method of alignment when compared to a polypeptide selected from the group consisting of UDP-glucose dehydrogenase polypeptides of SEQ ID NOs:2, 4, 6 and 8. The present invention also relates to an isolated polynucleotide comprising the complement of the nucleotide sequences described above.

It is preferred that the isolated polynucleotides of the claimed invention consists of a nucleic acid sequence selected from the group consisting of SEQ ID NOs:1, 3, 5 and 7 that codes for the polypeptide selected from the group consisting of SEQ ID NOs:2, 4, 6 and 8. The present invention also relates to an isolated polynucleotide comprising a nucleotide sequences of at least one of 40 (preferably at least one of 30) contiguous nucleotides derived from a nucleotide sequence selected from the group consisting of SEQ ID NOs:1, 3, 5 and 7 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a UDP-glucose dehydrogenase polypeptide of at least 480 amino acids comprising at least 94%, preferably 96% homology based on the Clustal method of alignment compared to a polypeptide selected from the group consisting of SEQ ID NOs:2, 4, 6 and 8 .

The present invention relates to a method of selecting an isolated polynucleotide that affects the level of expression of a UDP-glucose dehydrogenase polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level a UDP-glucose dehydrogenase polypeptide in the host cell containing the isolated polynucleotide; and comparing the level of a UDP-glucose dehydrogenase polypeptide in the host cell containing the isolated polynucleotide with the level of a UDP-glucose dehydrogenase polypeptide in a host cell that does not contain the isolated polynucleotide.

The present invention relates to a method of obtaining a nucleic acid fragment encoding a substantial portion of a UDP-glucose dehydrogenase polypeptide gene, preferably a plant UDP-glucose dehydrogenase polypeptide gene, comprising the steps of: synthesizing an oligonucleotide primer comprising a nucleotide sequence of at least one of 40 (preferably at least one of 30) contiguous nucleotides derived from a nucleotide sequence selected from the group consisting of SEQ ID NOs:1, 3, 5 and 7 and the complement of such nucleotide sequences; and amplifying a nucleic acid fragment (preferably a cDNA inserted in a cloning vector) using the oligonucleotide primer. The amplified nucleic acid fragment preferably will encode a portion of a UDP-glucose dehydrogenase amino acid sequence.

The present invention also relates to a method of obtaining a nucleic acid fragment encoding all or a substantial portion of the amino acid sequence encoding a UDP-glucose dehydrogenase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a UDP-glucose dehydrogenase, the method comprising the steps of: (a) transforming a host cell with a chimeric gene comprising a nucleic acid fragment encoding a UDP-glucose dehydrogenase, operably linked to suitable regulatory sequences; (b) growing the transformed host cell under conditions that are suitable for expression of the chimeric gene wherein expression of the chimeric gene results in production of UDP-glucose dehydrogenase in the transformed host cell; (c) optionally purifying the UDP-glucose dehydrogenase expressed by the transformed host cell; (d) treating the UDP-glucose dehydrogenase with a compound to be tested; and (e) comparing the activity of the UDP-glucose dehydrogenase that has been treated with a test compound to the activity of an untreated UDP-glucose dehydrogenase, thereby selecting compounds with potential for inhibitory activity.

The present invention also relates to a composition comprising an isolated polynucleotide comprising a nucleotide sequence encoding a first polypeptide of at least 70 amino acids that has at least 94% identity based on the Clustal method of alignment when compared to a polypeptide selected from the group consisting of UDP-glucose dehydrogenase polypeptides of SEQ ID NOs:2 and 4, or an isolated polynucleotide comprising the complement of the nucleotide sequence.

The present invention also relates to an expression cassette comprising an isolated polynucleotide of the present invention operably linked to a promoter.

The present invention also relates to a method for positive selection of transformed cell comprising:

(a) transforming a plant cell with a chimeric gene of the present invention or an expression cassette of the present invention; and (b) growing the transformed plant cell, preferably a monocot (such as corn), under conditions allowing expression of the polynucleotide in an amount sufficient to enhance plant growth to provide a positive selection means.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as partial cDNA clones ("EST"), the entire cDNA sequences of the indicated cDNA clones ("FIS"), DNA sequences assembled from two or more partial cDNA clones ("Contig"), DNA sequences assembled from an FIS and one or more ESTs ("Contig*"), or sequences encoding the entire protein derived from an FIS, a contig, or an FIS and PCR ("CGS"). Nucleotide SEQ ID NOs:5 and 7 and amino acid SEQ ID NOs:6 and 8 were determined by further sequence analysis of cDNA clones encoding the amino acid sequences set forth in SEQ ID NOs:2 and 4. Nucleotide SEQ ID NOs:1 and 3 and amino acid SEQ ID NOs:2 and 4 were presented in a U.S. Provisional Application No. 60/107,274, filed Nov. 5, 1998.

The sequence descriptions and Sequence Listing attached hereto comply with the rules governing nucleotide and/or amino acid sequence disclosures in patent applications as set forth in 37 C.F.R. §1.821–1.825.

TABLE 1

Proteins Involved in Hemicellulose Production

| Protein | Clone Designation | SEQ ID NO: (Nucleotide) | SEQ ID NO: (Amino Acid) |
|---|---|---|---|
| UDP-Glucose Dehydrogenase | rr1.pk077.el (EST) | 1 | 2 |
| UDP-Glucose Dehydrogenase | wlmk8.pk0004.f6 (EST) | 3 | 4 |
| UDP-Glucose Dehydrogenase | rr1.pk077.el (FIS) | 5 | 6 |
| UDP-Glucose Dehydrogenase | wlmk8.pk0004.f6 (FIS) | 7 | 8 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least one of 40 contiguous nucleotides, preferably at least one of 30 contiguous nucleotides, most preferably one of at least 15 contiguous nucleotides, of the nucleic acid sequence of the SEQ ID NOs:1, 3, 5 and 7.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 40 (preferably at least one of 30, most preferably at least one of 15) contiguous nucleotides derived from a nucleotide sequence selected from the group consisting of SEQ ID NOs:1, 3, 5 and 7 and the complement of such nucleotide sequences may be used in methods of selecting an isolated polynucleotide that affects the expression of a polypeptide in a plant cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are 80% identical to the amino acid sequences reported herein. Preferred nucleic acid fragments encode amino acid sequences that are 85% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Suitable nucleic acid fragments not only have the above homologies but typically encode a polypeptide having at least 50 amino acids, preferably 100 amino acids, more preferably 150 amino acids, still more preferably 200 amino acids, and most preferably 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several proteins involved in hemicellulose production have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other UDP-glucose dehydrogenase enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA*

86:5673–5677;Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 40 (preferably one of at least 30, most preferably one of at least 15) contiguous nucleotides derived from a nucleotide sequence selected from the group consisting of SEQ ID NOs:1, 3, 5 and 7 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as UDP-glucose dehydrogenase) preferably a substantial portion of a plant polypeptide of a gene, comprising the steps of: synthesizing an oligonucleotide primer comprising a nucleotide sequence of at least one of 40 (preferably at least one of 30, most preferably at least one of 15) contiguous nucleotides derived from a nucleotide sequence selected from the group consisting of SEQ ID NOs:1, 3, 5 and 7 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen eDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of altering the level of UDP-glucuronic dehydrogenase production in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or co-suppression (U.S. Pat. Nos. 5,190,931, 5,107,065 and 5,283,323). An antisense or co-suppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded protein involved in hemicellulose production. An example of a vector for high level expression of the instant polypeptides in a bacterial host is provided (Example 6).

Additionally, the instant polypeptides can be used as a targets to facilitate design and/or identification of inhibitors of those enzymes that may be useful as herbicides. This is desirable because the polypeptides described herein catalyze various steps in the production of hemicellulose. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet*. 35 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet*. 7:149–154). Although current methods of FISH mapping favor use of large clones (several to several hundred KB; see Laan et al. (1995) *Genome Res*. 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med*. 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res*. 18:3671), Radiation Hybrid Mapping (Walter et al. (1997) *Nat. Genet*. 7:22–28) and Happy Mapping (Dear and Cook (1989) *Nucleic Acid Res*. 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various rice and wheat tissues were prepared. The characteristics of the libraries are described below.

TABLE 2 cDNA Libraries from Rice and Wheat

| Library | Tissue | Clone |
|---|---|---|
| rr1 | Rice root of two week old developing seedling | rr1.pk077.e1 |
| wlmk8 | Wheat seedlings 8 hours after inoculation with *Erysiphe graminis* f. sp *tritici* and treatment with a fungicide * | wlmk8.pk0004.f6 |

* Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding proteins involved in hemicellulose production were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding UDP-Glucose Dehydrogenase

The BLASTX search using the designated sequences from clones listed in Table 3 revealed similarity of the polypeptides encoded by the cDNAs to UDP-glucose dehydrogenase from Glycine max (NCBI Identifier No. gi 1518540). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to Glycine max UDP-Glucose Dehydrogenase

| Clone | Status | BLAST pLog Score to gi 1518540 |
|---|---|---|
| rr1.pk077.e1 | (FIS) | >254.00 |
| wlmk8.pk0004.f6 | (FIS) | >254.00 |

The data in Table 4 represents a calculation of the percent identity of the amino acid sequences set forth in SEQ ID NOs:2, 4 and 6 and the Glycine max sequence.

TABLE 4

Percent Identity of Amino Acid Sequences Deduced From the Nucleotide Sequences of cDNA Clones Encoding Polypeptides Homologous to Glycine max UDP-Glucose Dehydrogenase

| SEQ ID NO. | Percent Identity to gi 1518540 |
|---|---|
| 6 | 90% |
| 8 | 90% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a UDP-glucose dehydrogenase. These sequences represent the first rice and wheat sequences encoding UDP-glucose dehydrogenase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A Du Pont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al.(1985) Nature 313:810–812), the hygromycin phosphotransferase gene from plasmid pJR225 (from *E. coli*; Gritz et al.(1983) Gene 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of Proteins Involved in Hemicellulose Production The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for UDP-glucose dehydrogenase are presented by Tenhaken et al., (1996) Plant Physiol. 112(3): 1127–1134.

What is claimed is:

1. An isolated polynucleotide comprising:
   (a) a nucleotide sequence encoding a polypeptide having UDP-glucose dehydrogenase activity, wherein the amino acid sequence of the polypeptide and the amino acid sequence of SEQ ID NO:8 have at least 96% identity based on the Clustal alignment method, or
   (b) the complement of the nucleotide sequence of (a).

2. The polynucleotide of claim 1 comprising the nucleotide sequence of SEQ ID NO:7.

3. The polynucleotide of claim 1, wherein the polypeptide comprises the amino acid sequence of SEQ ID NO:8.

4. A chimeric gene comprising the polynucleotide of claim 1 operably linked to a regulatory sequence.

5. A vector comprising the polynucleotide of claim 1.

6. A method for transforming a cell comprising transforming a cell with the polynucleotide of claim 1.

7. A cell comprising the chimeric gene of claim 4.

8. A method for producing a plant comprising transforming a plant cell with the polynucleotide of claim 1 and regenerating a plant from the transformed plant cell.

9. A plant comprising the chimeric gene of claim 4.

10. A seed comprising the chimeric gene of claim 4.

11. A method for isolating a polypeptide encoded by the polynucleotide of claim 1 comprising isolating the polypeptide from a cell containing a recombinant DNA construct comprising the polynucleotide of claim 1, operably linked to a regulatory sequence.

* * * * *

UNITED STATES PATENT AND TRADEMARK OFFICE
CERTIFICATE OF CORRECTION

PATENT NO.    : 6,653,099 B1
DATED         : November 25, 2003
INVENTOR(S)   : Famodu et al.

Page 1 of 1

It is certified that error appears in the above-identified patent and that said Letters Patent is hereby corrected as shown below:

<u>Title page</u>,
Item [75], Inventors, please insert -- Saverio Carl Falco, Wilmington, DE (US) --.
Item [56], References Cited, please insert
-- U.S. PATENT DOCUMENTS
US20020061301, 05-2002, Bandman et al.* --.
OTHER PUBLICATIONS, please insert -- Alignment of SEQ ID NO. 7 from Bandman et al. to SEQ ID NO. 7 of instance application* --.

<u>Columns 21-22</u>
Bottom of columns, Sequence Listing section, please delete entire section beginning at bottom of columns 21 and 22 through top of columns 35 and 36 and replace with
-- Amended Sequence Listing filed on August 28, 2002 and entered December 3, 2002.--

<u>Column 36</u>,
Line 22, delete "," before the word "operably".

Signed and Sealed this

Twenty-second Day of February, 2005

JON W. DUDAS
*Director of the United States Patent and Trademark Office*